US009609866B2

(12) United States Patent
Devisetty et al.

(10) Patent No.: US 9,609,866 B2
(45) Date of Patent: Apr. 4, 2017

(54) PLANT GROWTH REGULATOR COMPOSITIONS, METHODS OF PREPARATION AND USE THEREOF

(71) Applicant: Valent BioSciences Corporation, Libertyville, IL (US)

(72) Inventors: Bala N. Devisetty, Buffalo Grove, IL (US); Heemanshubhai K. Patel, Des Plaines, IL (US); Dale O. Wilson, Jr., Round Lake Beach, IL (US); Peter D. Petracek, Grayslake, IL (US); Xiaozhong Liu, Vernon Hills, IL (US); Gregory D. Venburg, Deerfield, IL (US); Warren E. Shafer, Libertyville, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 24 days.

(21) Appl. No.: 14/665,263

(22) Filed: Mar. 23, 2015

(65) Prior Publication Data

US 2015/0189875 A1 Jul. 9, 2015

Related U.S. Application Data

(62) Division of application No. 13/598,884, filed on Aug. 30, 2012, now Pat. No. 9,023,762.

(60) Provisional application No. 61/529,345, filed on Aug. 31, 2011.

(51) Int. Cl.
| | | |
|---|---|---|
| *A01N 43/60* | (2006.01) | |
| *A01N 37/36* | (2006.01) | |
| *A01N 37/42* | (2006.01) | |
| *A01N 43/90* | (2006.01) | |

(52) U.S. Cl.
CPC ............ *A01N 37/36* (2013.01); *A01N 37/42* (2013.01); *A01N 43/90* (2013.01)

(58) Field of Classification Search
CPC ......... A01N 37/36; A01N 37/42; A01N 43/90
See application file for complete search history.

(56) References Cited

U.S. PATENT DOCUMENTS

| | | | |
|---|---|---|---|
| 3,927,205 | A | 12/1975 | Ohno et al. |
| 4,209,530 | A | 6/1980 | Visscher |
| 4,434,180 | A | 2/1984 | Visscher |
| 4,581,057 | A | 4/1986 | Nooden |
| 6,004,905 | A | 12/1999 | Abrams et al. |
| 6,884,754 | B1 | 4/2005 | Schlatter et al. |
| 6,984,609 | B2 | 1/2006 | Devisetty et al. |
| 2002/0028875 | A1 | 3/2002 | Anderle et al. |
| 2002/0042346 | A1 | 4/2002 | Hamersky et al. |
| 2002/0065198 | A1 | 5/2002 | Highsmith et al. |
| 2005/0025791 | A1 | 2/2005 | Remenar et al. |
| 2008/0207454 | A1 | 8/2008 | Heiman et al. |
| 2008/0254988 | A1 | 10/2008 | Wang et al. |
| 2009/0137391 | A1 | 5/2009 | Wilson et al. |
| 2010/0152046 | A1 | 6/2010 | Belkind et al. |
| 2010/0313620 | A1 | 12/2010 | Armbrust et al. |

FOREIGN PATENT DOCUMENTS

| | | |
|---|---|---|
| WO | WO 2008/094558 | 8/2008 |
| WO | WO 2008/156863 | 12/2008 |

OTHER PUBLICATIONS

EESR issued Feb. 16, 2015.
MedlinePlus, U.S. National Library of Medicine NIH National Institutes of Health, Antioxidants, last updated Aug. 20, 2013, topic reviewed Oct. 31, 2012, total pp. 6.
Chemical of the Week, Chelates and Chelating Agents, printed Sep. 1, 2013, total pp. 3.
Preservative—Wikipedia, the free encyclopedia, printed Sep. 1, 2013, total pp. 2.
Annual Book of ASTM Standards, Section Eleven Water and Environmental Technology, vol. 11.05, 2012, total pp. 2.
Dumitru et al., "The influence of rheology modifiers and dispersin agents on the quality of water-based decorative paints", Rev. Chem. (Bucharest) 61, No. 7, 2010, pp. 651-656.
OECD Monograph Guidance, Mar. 2001, total pp. 4.
Manual on Development and Use of FAO Specifications for Plant Protection Products, Jan. 1999, total pp. 8.
Cytokinins—Plant-Hormones.info, Sponsored by Mendipweb, printed Sep. 2, 2013, total pp. 2.
International Search Report and Written Opinion issued by the International Bureau on Jan. 7, 2013.
Cutler et al, "Formation and breakdown of ABA", Trends in Plant Science, Dec. 1999, vol. 4 No. 12, pp. 472-478.
Finkelstein et al., "Abscisic acid biosynthesis and response", The Arabidopsis Book, American Society of Plant Biologists 2002, pp. 1-52.

*Primary Examiner* — David Browe
(74) *Attorney, Agent, or Firm* — Wood, Phillips, Katz, Clark & Mortimer

(57) ABSTRACT

Suspension concentrate compositions are disclosed for delivering S-(+)-Abscisic acid either alone or in combination with a second plant growth regulator to crop seed prior to planting as well as for foliar, soil drench, in-furrow and sprench (foliar spray and soil drench) applications are disclosed. The compositions, when properly combined in an aqueous carrier and processed through wet milling to achieve the desired particle size, will result in stable compositions that are desirable for treating crop seeds.

19 Claims, No Drawings

PLANT GROWTH REGULATOR COMPOSITIONS, METHODS OF PREPARATION AND USE THEREOF

CROSS REFERENCE TO RELATED APPLICATIONS

This application is a divisional of U.S. application Ser. No. 13/598,884, filed Aug. 30, 2012 which claims the benefit of U.S. Provisional Application No. 61/529,345, filed Aug. 31, 2011, which are incorporated herein by reference.

FIELD OF THE INVENTION

The present invention relates to plant growth regulator compositions, methods of their preparation, and methods of their use.

BACKGROUND OF THE INVENTION

Plant growth substances (e.g., plant hormones, phytohormones, or growth regulators) influence a range of plant developmental processes including stem elongation, germination, dormancy, flowering, sex expression, enzyme induction, fruit set and quality, as well as leaf and fruit senescence. S-(+)-Abscisic acid is a naturally-occurring hormone found in all higher plants (Cutler and Krochko, *Formation and Breakdown of ABA*, Trends in Plant Science, 4:472-478 (1999); Finkelstein and Rock, *Abscisic acid Biosynthesis and Signaling*, The Arabidopsis Book, ASPB, Monona, Md., 1-52 (2002)). S-(+)-Abscisic acid is reported to be found in all photosynthetic organisms (Cutler and Krochko, 1999; Finkelstein and Rock, 2002). S-(+)-Abscisic acid is involved in many major events of plant growth and development including dormancy, germination, bud break, flowering, fruit set, general growth and development, stress tolerance, ripening and abscission.

Commercial formulations comprising abscisic acid are used in agriculture for various purposes, such as improving stress tolerance, slowing growth rate, adjusting flowering phase and other purposes. Abscisic acid has also been reported to possess insect inhibition qualities (see U.S. Pat. Nos. 4,434,180 and 4,209,530).

S-(+)-Abscisic acid may be combined with a cytokinin such as benzyladenine. Treating a seed with benzyladenine has been shown to improve the emergence rate of seeds treated with S-(+)-Abscisic acid (see U.S. Patent Publication No. 2009/0137391).

Crop management comprises many aspects such as treating seed prior to planting, treating crops during various phases of plant growth (foliar or drench application) and post-harvest application to extending shelf-life.

Seed treatment has been found to be beneficial for hundreds of years. Seed treatment is gaining importance in the farming community as the cost of seed (including genetically modified seed) is on the rise increasing the need to protect seeds during storage as well as to protect them from adverse environmental conditions after planting and during germination or emergence of seedlings. Seed treatment includes coating seed with various pesticides including but not limited to fungicides, herbicides, insecticides, plant growth regulators and other nutrients. One of the major roles of seed treatment is to minimize the economic impact that might occur due to potential infestation and adverse growth conditions that could result in reduced yields as well as lower product/grain quality. Crop seed treated with various pesticides and plant growth enhancers include cereals (e.g., corn, sorghum, and wheat), legumes (e.g., soybean, peanut, and various beans) and vegetables (e.g., carrot, spinach, and tomato).

Topical (foliar) applications and or drench applications are carried out to protect growing crops from diseases and pests as well as to improve crop growth, yield and quality.

Plant growth regulators may be formulated in at least six different types of formulations: (1) solutions; (2) wettable powders; (3) soluble powders; (4) tablets; (5) water-dispersible granules; and (6) water soluble granules. In order to use such formulations, they must be diluted in an aqueous medium prior to conventional spray application. Each of the conventional types of formulations has disadvantages, therefore, research to develop improved delivery systems for plant growth regulators continues. Some of the disadvantages of conventional formulations with specific reference to abscisic acid are discussed below.

One of the problems associated with current abscisic acid formulations for use in agriculture is the relatively poor solubility of abscisic acid in water: only about 3 grams per liter, or alternatively, 0.3% by weight can be dissolved in water. A concentration of about 3000 ppm is the highest concentration that can be achieved in pure water at room temperature. Abscisic acid solubility in hard water (water with a high mineral content) is even less. These low strength solution formulations (which contain a low concentration of abscisic acid) require larger packaging, more storage space, and higher associated transportation, warehousing, and container disposal costs. Further, these formulations are not suitable for use in seed treatment because excessive carrier from the formulation may make the treated seed sticky and not suitable for conventional planters. In addition, higher seed moisture can also encourage mold growth and impair germination. These problems might increase as the formulation is tank-mixed with other seed treatment formulations containing insecticide(s) and fungicide(s). While abscisic acid exhibits somewhat better solubility in some organic solvents, liquid formulations of abscisic acid in organic solvents are often undesirable due to flammability, toxicity, or pollution considerations. In addition, abscisic acid is known to exhibit poor storage stability in solvent based formulations, cause hydroxylation inactivation of 8' and 9' methyl groups in plants (see U.S. Pat. No. 6,004,905) and cause sunlight induced degradation and isomerization of active 2-cis, 4-trans-S-(+)-Abscisic acid to the inactive 2-trans, 4-trans-S-(+)-Abscisic acid isomer (Kamuro, *The Present Situation and Problems in the R&D for Practical Uses of Abscisic Acid*, Plant and Chemical Regulation, 29:155-165 (1994)). Organic solvents may also exhibit an adverse effect on seed germination.

A soluble powder formulation is one which, when mixed with water, dissolves readily in water and forms a true solution. Once the solution is formed, no further mixing or agitation of the solution is required.

A wettable powder formulation is a dry, finely ground formulation. In this formulation, the active ingredient is combined with a finely ground dry carrier, usually a mineral clay, along with other ingredients that enhance the ability of the powder to be suspended in water. Upon mixing the wettable powder with water, a suspension is formed which is then applied to crops by spray equipment.

The primary disadvantage of wettable powder and soluble powder formulations is that they tend to produce dust upon handling, such as when pouring, transferring or measuring them. This dust may pose health hazards. Further, powder formulations tend to wet poorly and also solubilize slowly upon addition to water. Powder formulations thus take longer to wet, disperse, and solubilize in the tank-mix. Formation of lumps or partially solubilized spray solutions will lead to uneven distribution of the plant growth regulator with the potential for reduced field performance. Wettable powder formulations will also leave undesirable insoluble residues both in storage tanks and on sprayed foliage and fruit.

Tablet formulations are pre-measured dosage delivery systems. They are useful in small areas, or for ornamental purposes. Tablet formulations may be effervescent, and dissolve in water over a period of two to ten minutes depending upon the type and size of the tablet. However, tablets deliver only between 0.1-1 g of active ingredient per tablet and, therefore, are not an ideal product form.

Water dispersible granules are also known as wettable granules or dry flowables. This type of formulation is similar to a wettable powder, except that the active ingredient is formulated in the form of water dispersible granule. Water dispersible granules upon addition to water and mixing form suspensions. The resulting suspension must be agitated for a period of time in order to fully disperse the active ingredient. Agitation or by-pass recirculation of the formulation must also be maintained during application to ensure uniform suspension and spray coverage. The quality of water dispersible granules is highly dependent on the manufacturing process and the active-ingredient; and can result in low yield recoveries, poor attrition resistance leading to dust potential, high manufacturing cost and poor dispersion. Generally, sprays of dispersed water-dispersible granular formulations leave undesirable insoluble residues on the treated foliage and fruit. Water-dispersible granules may not be directly added to seed treatment mixtures and generally pre-mixing in a small portion of water may be necessary. Water-dispersible granules can become hardened over time, thus resulting in poor dispersibility and solubility of the active ingredient. Dust and caking may be problems with certain water-dispersible granules and powder formulations. Water-dispersible granules may thus not be ideal product forms for seed treatment.

A soluble granule formulation is one which, when mixed in water, dissolves readily in water and forms a true solution. Once the solution is formed, no further mixing or agitation of the tank-mix is required. U.S. Pat. No. 6,984,609 B2 discloses water-soluble granular compositions of at least one plant growth regulator, preferably a gibberellin, a disaccharide and a surfactant. U.S. Patent Application Publication No. 2008/0254988 discloses a composition for a 5% solution formulation as well as a 20% water soluble granular formulation for S-(+)-Abscisic acid. The granules must be solubilized in water prior to addition to seed and foliar treatment mixtures. However, the solubility limit of S-(+)-Abscisic acid in the tank-mix is only up to 3000 ppm. Thus, this type of formulation is not ideal for S-(+)-Abscisic acid and its use in seed-treatment mixtures.

Therefore, there is still a need for an S-(+)-Abscisic acid formulation that overcomes the disadvantages of the prior art formulations.

SUMMARY OF THE INVENTION

In a first aspect, the present invention is generally directed toward S-(+)-Abscisic acid compositions in an aqueous suspension concentrate form. The S-(+)-Abscisic acid compositions overcome the disadvantages of the prior art because they are concentrated, stable and highly effective. These qualities also make the compositions more cost effective.

The S-(+)-Abscisic acid compositions also are versatile because they can be used for commercial seed treatment, foliar, drench, in-furrow and sprench (foliar spray and soil drench) applications.

Further, the compositions of the present invention are liquid compositions that are safer for the environment than many prior art formulations because they contain low amounts of Volatile Organic Compounds (VOC) and, therefore, satisfy environmental and regulatory requirements in areas in which they are most needed.

Another important feature is that the compositions of the present invention do not harm germinating seeds or seedlings and accordingly are suitable for commercial applications.

In a suspension concentrate, the S-(+)-Abscisic acid is in a suspended state as micro particles. In some embodiments, the majority ($D_V90$ or 90%) of the micro S-(+)-Abscisic acid particles should be less than 10 micrometers in diameter (e.g., from about 10 to about 0.01 micrometers). Preferably, the median volume diameter of the particles should be from about 2 to about 5 micrometers.

In some embodiments of the invention, the compositions include from about 5 to about 40% S-(+)-Abscisic acid suspended as micro particles; from about 0.1 to about 1.0% of at least one non-ionic polymeric surfactant that is a difunctional block copolymer surfactant with terminal secondary hydroxyl groups; from about 0.5 to about 4.0% of at least one non-ionic polymeric surfactant that is a difunctional block copolymer surfactant with terminal primary hydroxyl groups; from about 0.5 to about 5.0% of at least one vinylpyrrolidone/vinylacetate copolymer wherein the molar ratio of vinylpyrrolidone to vinylacetate is from about 30:70 to about 70:30; from about 5 to about 20% of at least one diol; from about 0.045 to about 0.2% of at least one rheological modifier; from about 0.3 to about 0.5% of at least one silicone anti-foaming agent; at least one preservative; at least one chelating agent; and at least one antioxidant, wherein all percentages are based on the total weight of the composition.

Each of the components of the composition contributes to the stability and effectiveness of the composition. Applicants found that the amounts of the non-ionic polymeric surfactant that is a difunctional block copolymer surfactant with terminal secondary hydroxyl groups, the non-ionic polymeric surfactant that is a difunctional block copolymer surfactant with terminal primary hydroxyl groups, vinylpyrrolidone/vinylacetate copolymer, the rheological modifier; and the anti-foaming agent where particularly important to the formulation (for example, compare Examples 2 to 5 with Example 6).

Further, Applicants found that the molar ratio of the vinylpyrrolidone to vinylacetate copolymer was critical for proper performance of the formulation.

In addition, Applicants found that use of a silicone based anti-foaming agent was important for the formulation to have the appropriate physical properties.

Applicants' compositions include stable and improved S-(+)-Abscisic acid compositions with as much as 40% active. Applicants have exemplified herein formulations at approximately 25%, 10%, and 5% S-(+)-Abscisic acid. Users of plant growth regulators may use Applicants' teachings herein to create formulations with any amount of S-(+)-Abscisic acid from at least 5% to at least 40%.

In a second aspect, the invention provides a method for making such compositions. In one embodiment, the components of the instant formulation are combined in an aqueous carrier and milled.

In a third aspect, the invention provides methods of using said compositions to treat either seeds or crops. In some embodiments, the suspension concentrates of the present invention may either be used directly in treating crop seeds or combined with other insecticides, fungicides, colorants and polymeric compositions prior to treating seeds. The suspension concentrates may also be diluted in water and used in foliar or soil drench, in-furrow and or sprench (foliar spray with a soil drench) applications.

DETAILED DESCRIPTION OF THE INVENTION

It is an object of the present invention to provide concentrated, stable and efficacious, and cost effective S-(+)-Abscisic acid suspension compositions for commercial seed treatment, foliar, drench, in-furrow and sprench (foliar spray and soil drench) applications. The compositions of the invention incorporate low Volatile Organic Compounds (VOC) to meet both environmental and regulatory requirements. The compositions of the invention also are not injurious to germinating seedlings and are suitable for treating seed in commercial seed treaters.

It has been discovered that specific compositions of microparticles suspended and stabilized exhibit improved properties of S-(+)-Abscisic acid. The suspension compositions can be applied directly to seeds or mixed with other mixtures that may contain an insecticide, a fungicide, or other adjuvants. The compositions of the invention do not exhibit significant settling and or separation upon storage. Furthermore, the compositions exhibit little or no phytotoxicity or other deleterious effects on germinating seedling and or growing plants.

In an embodiment of the invention, aqueous suspension concentrate compositions include: from about 5 to about 40% S-(+)-Abscisic acid suspended as micro particles; from about 0.1 to about 1.0% of at least one non-ionic polymeric surfactant that is a difunctional block copolymer surfactant with terminal secondary hydroxyl groups; from about 0.5 to about 4.0% of at least one non-ionic polymeric surfactant that is a difunctional block copolymer surfactant with terminal primary hydroxyl groups; from about 0.5 to about 5.0% of at least one vinylpyrrolidone/vinylacetate copolymer wherein the molar ratio of vinylpyrrolidone to vinylacetate is from about 30:70 to about 70:30; from about 5 to about 20% of at least one diol; from about 0.045 to about 0.2% of at least one rheological modifier; from about 0.3 to about 0.5% of at least one silicone anti-foaming agent; at least one preservative; at least one chelating agent; and at least one antioxidant, wherein all percentages are based on the total weight of the composition. Further, a sufficient amount of water may be added to the composition.

In further embodiment, the composition may include from about 20% to about 30% wt/wt of S-(+)-Abscisic acid.

In another embodiment, the composition may include from about 0.20 to about 0.60% wt/wt of at least one non-ionic polymeric surfactant that is a difunctional block copolymer surfactant with terminal secondary hydroxyl groups.

In yet another embodiment, the vinylpyrrolidone/vinylacetate copolymer is from about 0.8 to about 1.0% wt/wt of the composition.

In an embodiment, the rheological modifier is from about 0.05 to about 0.08% wt/wt of the composition.

In a further embodiment, the diol is selected from the group consisting of ethylene glycol, diethylene glycol, propylene glycol and hexylene glycol; the preservatives are selected from the group consisting of methyl p-hydroxy benzoate, propyl p-hydroxy benzoate and potassium sorbate; the chelating agent is selected from the group consisting of EDTA, EDTA salts, citrates and gluconates; the antioxidant is selected from the group consisting of propyl gallate, ascorbic acid and its salts and tert-butylhydroquinone; and the rheological modifier is a polysaccharide or cellulose derivative.

In another embodiment of the composition, the diol is propylene glycol; the polysaccharide is xanthan gum; and the anti-foaming agent is polydimethylsiloxane.

In a further embodiment of the composition, the preservatives are methyl p-hydroxy benzoate, propyl p-hydroxy benzoate, and potassium sorbate; the chelating agent is EDTA; and the antioxidant is propyl gallate.

In an embodiment of the composition, the composition may include: from about 20 to about 30% S-(+)-Abscisic acid; from about 0.3 to about 0.5% of a non-ionic polymeric surfactant that is a difunctional block copolymer surfactant with terminal secondary hydroxyl groups; from about 2.0 to about 4.0% of a non-ionic polymeric surfactant that is a difunctional block copolymer surfactant with terminal primary hydroxyl groups; from about 0.8 to about 1.0% of a vinylpyrrolidone/vinylacetate copolymer; from about 9.0 to about 11.0% propylene glycol; from about 0.05 to about 0.07% xanthan gum; from about 0.3 to about 0.5% polydimethylsiloxane; from about 0.1 to about 0.3% methyl p-hydroxy benzoate, from about about 0.08 to about 0.12% propyl p-hydroxy benzoate, from about 0.2 to about 0.40% potassium sorbate; from about 0.1 to about 0.3% EDTA; and from about 0.8 to about 0.12% propyl gallate; wherein all percentages are based on the total weight of the composition. Further, a sufficient amount of water may be added to the composition.

In yet another embodiment, the composition may include: about 25% S-(+)-Abscisic acid; about 0.40% of a non-ionic polymeric surfactant that is a difunctional block copolymer surfactant with terminal secondary hydroxyl groups; about 3.00% of a non-ionic polymeric surfactant that is a difunctional block copolymer surfactant with terminal primary hydroxyl groups; about 0.90% vinylpyrrolidone/vinylacetate copolymer; about 10.00% propylene glycol; about 0.06% xanthan gum; about 0.42% polydimethylsiloxane; about 0.20% methyl p-hydroxy benzoate, about 0.10% propyl p-hydroxy benzoate, about 0.30% potassium sorbate; about 0.20% EDTA; and about 0.10% propyl gallate; wherein all percentages are based on the total weight of the composition. Further, a sufficient amount of water may be added to the composition.

In a further embodiment, the suspension concentrate comprises a cytokinin. The weight ratio of S-(+)-Abscisic acid to the cytokinin can be from about 5:1 to about 40:1 and the cytokinin may be 6-benzyladenine.

In a further embodiment, the invention is directed to a method of treating a seed comprising applying an effective amount of a composition of the invention to the seed.

In further embodiments, the seed may be a corn, sorghum, barley, wheat, rice, canola, soybean, peanut, sunflower, various beans, carrot, spinach, tomato or other crop seed or a propagule of agronomic interest.

In another embodiment, the compositions may be applied to male inbred corn line seeds to alter the timing of germination and tassel development of the seeds to facilitate hybrid seed production.

In a specific embodiment, the composition may be applied to canola seeds and other crop seeds of agronomic interest to achieve a desired germination delay which will result in a higher emergence rate.

In yet another embodiment, the invention is directed to a method of regulating germination by treating a seed with effective amounts of compositions of the invention.

In a further embodiment, the invention is directed to methods of improving drought stress tolerance, shelf life, quality and yield of agronomic and horticultural important crops.

The compositions of the present invention can be applied by foliar, drench, in-furrow or sprench application.

In any of the methods of the invention the seeds include, but are not limited to, corn, sorghum, wheat, rice/paddy, canola, soybean, peanut, various beans, carrot, spinach, tomato seed or other crops of agronomic interest.

In any of the methods of the invention, a further agrochemical formulation can be applied in combination with the compositions of the invention. Such further agrochemical formulation may comprise insecticides, fungicides, plant growth regulators, nutrients or other adjuvants. The agrochemical formulation can be applied directly to the seeds or agricultural or horticultural crops of interest before, after or simultaneously with the composition of the invention. Further agrochemical formulations can also be mixed with the compositions of the invention and applied to the seeds or agricultural or horticultural crops of interest.

The trade names used herein often are common to a class or series of respective components. Therefore, when a trade name is mentioned, any component in the family including the trade name will be suitable.

The terms "composition" and "formulation" are used interchangeably throughout the application.

In each embodiment of the invention, a sufficient amount of water may be added. When used herein, the phrase "sufficient amount of water" refers to the amount of water that may be added to impart the desired qualities, such as viscosity, to the composition.

As used herein, all numerical values relating to amounts, weight percentages and the like, are defined as "about" or "approximately" each particular values plus or minus 10% (±10%). For example, the phrase "greater than 0.1%" is to be understood as encompassing values greater than 0.09%. Therefore, amounts within 10% of the claimed values are encompassed by the scope of the invention.

The composition is an aqueous suspension concentrate comprising S-(+)-Abscisic acid suspended as micro particles. As used herein, the term "aqueous suspension concentrate" refers to a stable suspension of active ingredient(s) with water as the fluid, intended for dilution with water before use (Manual on Development and use of FAO and WHO specifications for pesticides, Appendix E: CropLife International Codes for Technical and Formulated Pesticides).

S-(+)-Abscisic acid is well understood to one versed in the art and is clearly intended to include derivatives and racemic mixtures of abscisic acid. The concentration of S-(+)-Abscisic acid in the compositions may range between about 5% wt/wt to about 40% wt/wt. Preferably, the concentration of S-(+)-Abscisic acid in the formulation is from about 5% wt/wt to about 30% wt/wt, more preferably from about 20 to 30% wt/wt. Most preferably, the concentration of S-(+)-Abscisic acid in the formulation is 25% wt/wt. The concentration of the S-(+)-Abscisic acid can also be at about 5% (with a preferred range of from about 3 to about 7%) or 10% (with a preferred range of from about 8 to about 12%), depending on the users' needs.

As used herein, the term "S-(+)-Abscisic acid" includes analogs of the acid.

Presently preferred ABA analogs include PBI-425, PBI-429, PBI-524, PBI-696, and PBI-702.

For the purposes of this Application, abscisic acid analogs are defined by Structures 1, 2, and 3, wherein for Structure 1:
the bond at the 2-position of the side chain is a cis- or trans-double bond,
the bond at the 4-position of the side chain is a trans-double bond or a triple bond,
the stereochemistry of the alcoholic hydroxyl group is S-, R- or an R,S-mixture,
the stereochemistry of the R1 group is in a cis-relationship to the alcoholic hydroxyl group,
R1 is ethynyl, ethenyl, cyclopropyl, or trifluoromethyl, and
R2 is hydrogen or lower alkyl

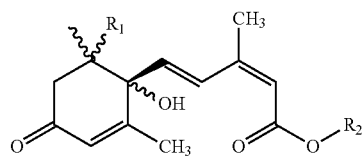

Structure 1 wherein lower alkyl is defined as an alkyl group containing 1 to 4 carbon atoms in a straight or branched chain, which may comprise zero or one ring or double bond when 3 or more carbon atoms are present.

For PBI-429, R1 is ethynyl, and R2 is a methyl group. PBI-429 is racemic.

For PBI-425, R1 is ethynyl, the orientation of the bonds for R1 and the hydroxyl group relative to the ring is alpha- in both cases, and the terminal carboxyl group is in the Z-orientation.

For PBI-524, R1 is ethynyl, and R2 is hydrogen. PBI-524 is racemic.

For PBI-696, R1 is cyclopropyl, and R2 is a methyl group. PBI-696 is racemic.

For Structure 2:
the bond at the 2-position of the side chain is a cis- or trans-double bond,
the bond at the 4-position of the side chain is a triple bond,
the stereochemistry of the alcoholic hydroxyl group is S-, R- or an R,S-mixture,
R1 is hydrogen or lower alkyl

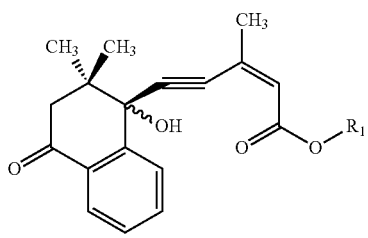

Structure 2 wherein lower alkyl is defined as an alkyl group containing 1 to 4 carbon atoms in a straight or branched chain, which may comprise zero or one ring or double bond when 3 or more carbon atoms are present.

For PBI-702, R1 is a methyl group.

For Structure 3:
the bond at the 2-position of the side chain is a cis- or trans-double bond,
the bond at the 4-position of the side chain is a trans-double bond,
the stereochemistry of the alcoholic hydroxyl group is S-, R- or an R,S-mixture,
R1 is hydrogen or lower alkyl Structure 3

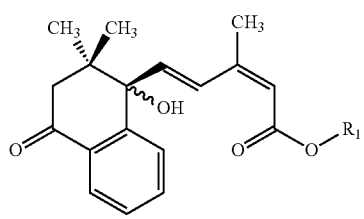

wherein lower alkyl is defined as an alkyl group containing 1 to 4 carbon atoms in a straight or branched chain, which may comprise zero or one ring or double bond when 3 or more carbon atoms are present.

Salts of the above abscisic acid analogs including the sodium and potassium salts may be used in this invention. Salts of abscisic acid including the sodium and potassium salts may also be used in this invention.

The compositions of the invention provide advantages such as wetting, spreading, adhesion, coating property, chemical compatibility, storage stability, dilution stability and ecological and handler safety. The compositions also eliminate settling issues and crystal growth that are commonly observed in suspension concentrates having high active ingredient concentrations. Aqueous based compositions offer further advantages such as ease of measuring and dilution to the desired spray concentration.

The viscosity of a composition is dependent upon the components utilized in the composition, process, instrumentation, and measurement methods. The preferred compositions of the application, however, should have a viscosity range of 200 to 400 cP when measured under ambient conditions. This viscosity range will allow for a flowable composition that can be easily handled, mixed and applied, while maintaining suspension stability (i.e. doesn't cake or have significant bleed). Embodiments of the invention may contain a sufficient amount of water to provide the desired properties, including the desired viscosity.

In some embodiments, the compositions of the invention further comprise a cytokinin such as 6-benzylaminopurine (i.e., 6-benzyladenine), kinetin, zeatin, thidazuron, and forchlorfenuron, preferably the cytokinin is 6-benzyladenine or kinetin. A preferred composition of this invention contains S-(+)-Abscisic acid or an analog thereof with a cytokinin wherein the weight ratio of the S-(+)-Abscisic acid or an analog thereof to the cytokinin is from about 5:1 to about 40:1, more preferably the ratio of S-(+)-Abscisic acid or an analog thereof to cytokinin is from about 25:1 to about 30:1. In some embodiments the preferred cytokinin is 6-benzyladenine.

As used in the present invention, the term "preservative" means any natural or synthetic chemical compound or substance that is added to prevent decomposition of the active ingredient by microbial growth or by undesirable chemical reactions. These preservatives may also protect the composition from undesirable changes in physical properties such as viscosity, color, pH etc. The preservatives may include, but are not limited to, antimicrobial preservatives which inhibit growth of bacteria, fungi, antioxidants that inhibit or retard oxidation of a molecule or a substance, and chelating agents that bind strongly with metal ions. Antimicrobials may include, but are not limited to, ascorbic acid, sodium or calcium ascorbate, benzoic acid, sodium or potassium benzoate, methyl paraben, propyl paraben, sorbic acid, potassium sorbate, citric acid and tartaric acid. Antioxidants may include, but are not limited to, propyl gallate, butylated hydroxytoluene (BHT), butylated hydroxyanisol (BHA) and tert-butyl hrydroquinone (tBHQ). Chelating agents include, but are not limited to, tetrasodium ethylenediaminetetraacetate and tetrapotassium ethylenediaminetetraacetate.

Preservatives are added to the compositions of the invention in an effective amount. The phrase "effective amount" of a preservative means a nontoxic but sufficient amount of antimicrobial preservative, antioxidant, or chelating agent to exhibit the desired effect. The amount of preservative that is "effective" will vary from composition to composition, depending on the particular composition, the particular antimicrobial, antioxidant, chelating agent, and the like. An appropriate "effective amount" in any individual case may be determined by one of ordinary skill in the art using routine experimentation. This amount is generally at least about 0.001% wt/wt to about 1.0% wt/wt for antimicrobial agents, about 0.001% wt/wt to about 1.0% wt/wt for antioxidants, and about 0.01% wt/wt to about 1.0% wt/wt for chelating agents of the total weight of the composition.

In some embodiments, the compositions will include at least one antimicrobial agent including, but not limited to, potassium sorbate, methyl paraben (methyl p-hydroxy benzoate), and propyl paraben (propyl p-hydroxy benzoate). In further embodiments, the compositions may include a chelating agent such as tetrasodium EDTA. In some embodiments, the compositions may include an antioxidant such as propyl gallate. In some embodiments, the concentration of antimicrobial agent might range about 0.001% to about 0.5% wt/wt of the composition.

The concentration of potassium sorbate may be from about 0.05% wt/wt to about 0.35% wt/wt, preferably from about 0.25 to 0.35%, and is highly preferred at about 0.30% wt/wt of the composition.

The concentration of methyl paraben may be from about 0.001% wt/wt to about 0.4% wt/wt, preferably from about 0.05% wt/wt to about 0.3 wt/wt, more preferably from about 0.15 to about 0.25%, and is highly preferred at about 0.20% wt/wt of the composition.

The concentration of propyl paraben may be from about 0.001% wt/wt to about 0.25% wt/wt, preferably from about 0.05% wt/wt to about 0.2 wt/wt, more preferably from about 0.05 to about 0.15%, and is highly preferred at about 0.10% wt/wt of the composition.

The concentration of tetrasodium EDTA in the formulation may be from about 0.01% wt/wt to about 0.5% wt/wt, preferably from about 0.05% wt/wt to about 0.2% wt/wt, more preferably from about 0.05% wt/wt to about 0.30% wt/wt, most preferrably from about 0.15% wt/wt to about 0.25% wt/wt, and is highly preferred at about 0.20% wt/wt.

The concentration of propyl gallate may be from about 0.001% wt/wt to about 0.5% wt/wt, preferably from about 0.05% wt/wt to about 0.3% wt/wt, more preferably from about 0.05% wt/wt to about 0.15% wt/wt, and is highly preferred at about 0.10% wt/wt of the composition.

In some embodiments, at least one surfactant may be added to the compositions as a wetting, solubilizing, spreading and penetrating agent. The surfactant may also aid in suspension stabilization and desired rheological properties. Suitable surfactants include non-ionic surfactants, anionic surfactants, cationic surfactants, amphoteric surfactants, specialty and non-ionic polymeric surfactants or combinations thereof.

Non-ionic surfactant include, but are not limited to, ethoxylated sorbitan esters such as Emsorb, Tween®, and T-Maze; sorbitan fatty acid esters such as SPAN and Alkamuls®; ethoxylated alcohols such as Trycol®, Brij®, Armix, Plurafac® and Tergitol®; ethoxylated alkyl alcohols such as Tomadol®, ethoxylated vegetable oil such as Agnique®-SBO, CSO and RSO; sucrose and glucose esters and derivatives thereof such as Mazon®, Rheozan® and Glucopon®; ethoxylated alkyl phenols such as Igepal, Macol and Tergitol; ethoxylated fatty amines such as Trymeed and Ethomeen; ethoxylated fatty acids such as Emerset, Alkamul and Trydet; ethoxylated fatty esters such as Alkamul and Atlas™ G; fatty acids such as Atlas™ G-1556; glycerol esters such as Mazol GMO; glycol esters such as Glycol SEG; lanolin-based derivatives such as Amerchol CAB; methyl esters such as Oleocal ME; monoglycerides and derivatives such as Ethosperse G-26; propoxylated and ethoxylated fatty acids such as Antarox-AA 60; block copolymers of ethylene oxide and propylene oxide such as Pluronic® or Surfonic®; silicone-based surfactants such as Silwet, Breakthru and mixtures of organosilicone surfactant with non-ionic or ionic surfactants; polysaccharides, copolymers of acrylamide and acrylic acid; and acetylenic diol derivatives such as Surfynol 104 or tristyrylphenols such as Soprophor among others. Non-ionic surfactants can also include polyoxyethylene (20) monolaurate (i.e., Tween® 20 or polysorbate 20).

Silicone based surfactants include, but are not limited to, Silwet HS-312.

Anionic surfactants include, but are not limited to, modified styrene acrylic polymers such as Metasperse, phosphate esters such as Emphos and Rhodafac; dialkyl sulfosuccinates such as Monawet, N-acyl EDTA chelating surfactant (Hampshire) and N-acyl sarcosines (Hamposyl) among others. The concentration of anionic surfactant in the composition can range from about 0.05 wt/wt up to about 2.0% wt/wt.

Amphoteric surfactants include, but are not limited to, lecithin and lecithin derivatives; and imidazolines and imidazoline derivatives such as Miranol, among others.

Specialty and polymeric surfactants include, but are not limited to, Aersosol, Atlox, Snyperonic, Zephrym, and Metasperse. Such specialty and polymeric surfactants may also serve the function of crystal growth inhibition, dispersant, wetting aid and foliar penetrants. A presently preferred nonionic surfactant family is polyoxypropylene-polyoxyethylene block copolymers. Pluronic® 10R5, Pluronic® P104 and Pluraflo® L1060 are particularly preferred.

In some embodiments, the compositions will include an effective amount of two non-ionic surfactants: (1) a difunctional block copolymer surfactant with terminal secondary hydroxyl groups, wherein the effective amount is from about 0.1 to about 1.0% wt/wt; and (2) a difunctional block copolymer surfactant terminating in primary hydroxyl groups, wherein an effective amount is from about 0.5 to about 4.0% wt/wt. These surfactants surprisingly impart different but desirable properties.

The surfactant Pluronic® 10R5 imparts viscosity thus providing resistance to settling of solid particles and may be added to the composition at a concentration from about 0.1% to about 5%. Preferably it is added from about 0.1% to 2.5%, more preferably from about 0.1% to 1.0%, and most preferably from about 0.3% to about 0.7% wt/wt of the composition. When about a 20 to 30%, or 25% S-(+)-Abscisic acid or an analog thereof composition is prepared, Pluronic® 10R5 is highly preferred at about 0.40%. When about a 5% or about a 10% S-(+)-Abscisic acid or an analog thereof composition is prepared, Pluronic® 10R5 is highly preferred at about 0.60%.

Pluronic® P104 is added to the composition at a concentration from about 0.5% to about 5%, preferably from about 0.5% to about 3%, and more preferably from about 0.5% to about 4.0% wt/wt of the composition, to maintain flow property specifically upon long term storage. When about a 20 to 30%, or 25% S-(+)-Abscisic acid or an analog thereof composition is prepared, Pluronic® P104 is highly preferred at about 3.0% wt/wt of the composition. When about a 5% S-(+)-Abscisic acid or an analog thereof composition is prepared, Pluronic® P104 is highly preferred at about 0.60% wt/wt of the composition. When about a 10% S-(+)-Abscisic acid or an analog thereof composition is prepared, Pluronic® P104 is highly preferred at about 1.0% wt/wt of the composition.

In other embodiments, the compositions will include an effective amount of at least one binder or film former. The binder may include, but is not limited to, polyvinyl pyrrolidone, polyvinyl acetate, polyvinyl acetate phthalate, polyvinyl alcohol, polyvinyl alcohol (hydrolyzed), vinylpyrrolidone/vinylacetate copolymer, polyethylene glycol, polyethylene wax, starch, modified celluloses and gums etc. to name a few. Preferred binders include polyvinyl pyrrolidone such as Agrimer® 30, alkylated vinyl pyrrolidone copolymers such as Agrimer® AL-10 AND Agrimer® AL-10LC; cross-linked polyvinylpyrrolidones such as Agrimer® AT and Agrimer® ATF; copolymers of vinyl acetate and vinylpyrrolidone such as Agrimer® VA-6 and Agrimer® VA-7; lignosulfonates and sodium or calcium salts thereof such as Marasperse, Vanisperrse, Borresperse, Norlig®, and Kraftsperse; unsulfonated lignins such as Indulin AT; clays such as Bentonite, Montmorillonite, Hectorite, Hydrite RS, microcrystalline celluloses such as Avicel PH and Lattice Not; methyl cellulose ethers such Methocel; ethyl cellulose polymers such as Ethocel; starch (natural or modified); gluten, silicates and sodium or calcium salts thereof; magnesium aluminum silicates such as Veegum F; natural or modified lecithins such as Beakin, Centomix, or Yelkin; sugar alcohols such as Neosorb, Sorbogem, Manogem and Maltsweet, Maltodextrins such as Maltrin M100 and polyethylene glycols, among others. A presently preferred binder is copolymers of vinyl acetate and vinylpyrrolidone such as Agrimer® VA6.

In some embodiments, the preferred binder/film former is a vinylpyrrolidone/vinylacetate copolymer wherein the ratio of vinylpyrrolidone to vinylacetate in the copolymer is from about 30:70 to about 70:30 and wherein the concentration of binder/film former in the composition may range from about 0.1% wt/wt to about 5% wt/wt, preferably, from about 0.5% wt/wt to about 1.5% wt/wt, even more preferably, from about 0.80% wt/wt to 1% wt/wt, and highly preferred at about 0.90% wt/wt.

In a further embodiment, the compositions will include an effective amount of at least one rheological modifier. The rheological modifier may be any hydrocolloid such as an agar, alginate, carageenan, gellan gum, guar gum, pectin, or polysaccharide or cellulose derivates such as hydroxypropylcellulose, carboxymethylcellulose, methylcellulose, ethyl cellulose and methyl hydroxypropylcellulose, xanthan gum, exudate and other seed gums, and clay or modified clay. The effective amount of the at least one rheological modifier is from about 0.005% to about 0.50%, preferably from about 0.01% to about 0.30% wt/wt, and more preferably from about 0.03% to about 0.3% wt/wt.

Preferably, the rheological modifier is xanthan gum wherein the concentration of xanthan gum may range between about 0.005% to about 0.50%, preferably from about 0.01% to about 0.30% wt/wt, more preferably from about 0.03% to about 0.3% wt/wt. The most preferred amount of xanthan gum when a 20% to 30%, or about 25% S-(+)-Abscisic acid or analog thereof formulation is prepared is from about 0.045 to about 0.08% wt/wt, and highly preferred at about 0.06% wt/wt. When a 5% S-(+)-Abscisic acid or analog thereof formulation is prepared, xanthan gum is highly preferred at about 0.3% wt/wt. When a 10% S-(+)-Abscisic acid or analog thereof formulation is prepared, xanthan gum is highly preferred at about 0.16% wt/wt.

In some embodiments, the compositions include at least one anti-foaming agent such as a silicone antifoaming agent. The silicone antifoaming agent may include, but is not limited to, polydimethylsiloxane. In some embodiments, the compositions will contain an effective amount of polydimethylsiloxane by itself or in the form of an emulsion. The concentration of polydimethylsiloxane emulsion may range from about 0.01% to about 3.0% wt/wt of the composition, preferably about 0.01% to about 2.0% wt/wt, preferably from about 0.06% to about 1.5% wt/wt. While the concentration of polydimethylsiloxane in the emulsion may range between about 1.0% to about 30% wt/wt of the emulsion, preferably the polydimethylsiloxane is 30% wt/wt of the emulsion. A presently preferred silicone antifoaming agent is SAG 1572.

The concentration of SAG 1572 (100%) may be from about 0.6% to about 5.0% wt/wt, preferably about 1.0% to about 2.0% wt/wt, more preferably from about 0.4% to about 0.5% wt/wt, and highly preferred at about 0.42% wt/wt of the composition.

In an additional embodiment, the composition includes S-(+)-Abscisic acid: (i) Agrimer® VA6 as the vinylpyrrolidone/vinylacetate copolymer; (ii) Pluronic® 105R and Pluronic® P104 as the surfactant/wetting and suspending agents; (iii) propylene glycol as the diol; (iv) methyl p-hydroxy benzoate, propyl p-hydroxy benzoate, and potassium sorbate as the preservatives; (v) EDTA as the chelating agent; (vi) propyl gallate as the antioxidant; (v) xanthan gum as the rheological modifier; and (vi) SAG 1572 as the anti-foaming agent. The compositions may also contain a sufficient amount of water.

In some embodiments the compositions may include additional surface active agents, crystal growth inhibitors, stickers, spreaders, leaf penetrants, dispersants, a systemic acquired resistance inducer, anti-foaming agents, preservatives, pH regulators, solubilization agents, a humectant, a dye, U.V. (ultra-violet) protectants, a vehicle or other components which facilitate production, storage stability, product handling application and biological efficacy.

The present invention provides very stable concentrated aqueous based formulations for seed treatment, as well as for foliar, drench, in-furrow, and/or sprench (foliar spray and soil drench) applications. In some embodiments, the compositions of the invention are applied to a seed.

The invention is also directed to methods for regulating germination by treating a seed with effective amounts of composition of the invention either alone or in combination with commonly utilized seed treatment compositions that may contain an insecticide, a fungicide, nutrient, adjuvant, polymer, or other growth regulators. In some embodiments, the invention provides methods wherein the compositions are applied to male inbred corn lines seeds to program the seed germination and tassel development in hybrid seed production. In other embodiments, the invention provides methods wherein the compositions are applied to canola seeds to achieve desired germination delay with ultimate higher emergence.

The invention is also directed to methods of improving drought stress tolerance, shelf life, quality and yield of agronomic and horticultural important crops. In some embodiments, the methods comprise applying the compositions of the invention to seeds of the crops. In other embodiments, the methods comprise applying the compositions through foliar, soil drench or sprench application.

The present invention enhances the utilization of aqueous flowable suspension concentrate compositions for seed treatment by permitting concentrations up to at least 25% weight such that the composition at application use rates sticks well to treated seed and there is no potential dust-off during further handling. The composition can be accurately metered and applied exhibiting rapid adhesion, drying and uniform film composition on the treated seed.

The present invention is not limited to the particular embodiments and modes of operation described herein and it is possible to imagine a number of variations in the details without departing from the scope of this invention.

Components utilized in the invention are described in Table 1.

TABLE 1

Components Used to Develop the Preferred Aqueous Suspension Concentrates

| Component | Trade Name | Source | Purpose |
|---|---|---|---|
| S-(+)-Abscisic acid T.G.A.I. | S-Abscisic acid | Lomon Biotechnology | Active Ingredient |
| Potassium (E,E)-hexa-2,4-dienoate | Potassium sorbate | Daicel Chemical Industries, Ltd. | Preservative |
| Tetra sodium ethylene diamino tetraacetate (EDTA) | Trilon ® BX powder | BASF Corp | Chelating Agent |
| Benzoic Acid, 4-hydroxy-, methyl ester | Methyl paraben | Mallinckrodt Baker | Preservative |
| Propyl p-hydroxy benzoate | Propyl paraben | Mallinckrodt Baker | Preservative |
| Propylene glycol | Propylene glycol | Lyondell Chemical Corp | Solubilization aid, Antifreeze |

TABLE 1-continued

Components Used to Develop the Preferred Aqueous Suspension Concentrates

| Component | Trade Name | Source | Purpose |
|---|---|---|---|
| 3,4,5-trihydroxy Benzoic acid propyl ester | Propyl gallate | Spectrum Chemical Mfg. Corp. | Antioxidant |
| Methyl-oxirane polymer with oxirane | Pluronic ® 10R5 | BASF Corp. | Surfactant |
| Methyl-oxirane polymer with oxirane | Pluronic ® P104 | BASF Corp. | Surfactant |
| Methyl-oxirane polymer with oxirane | Pluraflo ® L1060 | BASF Corp. | Surfactant |
| Xanthan gum | OptiXan ® 40T | Archer Daniels Midland Co. | Rheological Additive |
| Polydimethyl siloxane antifoam emulsion | SAG 1572 | Momentive Performance Materials | Antifoam |
| Acetic acid ethenyl ester, polymer with 1-ethenyl-2-pyrrolidinone | Agrimer ® VA6 | International Specialty Products | Binder/Film former |
| 2-Pyrrolidinone, 1-ethenyl-, homopolymer | Agrimer ® 30 | International Specialty Products | Binder/Film former |
| Calcium lignosulfonate | Norlig ® A | Borregaard LignoTech | Binder/Dispersant |
| Polyoxyethylene (20) sorbitan monolaurate | Tween ® 20 | Croda Inc. | Surfactant |
| Modified Styrene acrylic polymer | Atlox Metasperse ™ 500L | Croda Inc. | Surfactant |
| 100% Active Silicone compound | Antifoam 100 FG | Harcros Chemicals | Antifoam |
| Sodium sulfite | Sodium sulfite | Esseco USA | Antioxidant |
| Trisodium 2-hydroxypropane-1,2,3-tricarboxylate | Trisodium citrate | Jungbunzlauer | Preservative |
| Potassium hydroxide solution (45% wt/wt) | Potassium hydroxide | VWR Scientific | Solubilizer |

Example 1

Compositions of 40% Wt/Wt S-(+)-Abscisic Acid Aqueous Solution Formulation for Seed Treatment (Table 2)

The potassium sorbate was solubilized in water followed by simultaneous addition of S-(+)-Abscisic acid and potassium hydroxide maintaining a pH<9.00 throughout. Upon complete solubilization of S-(+)-Abscisic acid the required amount of sodium sulfite and sodium citrate were added ensuring complete solubilization followed by addition of Tween® 20 and Agrimer® 30 and further mixing for 15 minutes. The final formulation was sieved through 325 mesh to remove any insoluble impurities. The suitability of the formulation composition was studied in corn seed treatment. In the tables that follow, "q.s." is an abbreviation for "quantity sufficient" which indicates that enough of the composition component was added to bring the composition to the indicated volume.

TABLE 2

Composition of 40% wt/wt S-(+)-Abscisic acid Aqueous Solution Formulation for Seed Treatment (Example 1)

| Component | % wt/wt |
|---|---|
| S-ABA (95.5% wt/wt pure) | 41.88 |
| Potassium hydroxide solution (45% wt/wt) | 16.99 |
| Sodium sulfite | 0.50 |
| Sodium citrate | 1.00 |
| Potassium Sorbate | 0.25 |
| Tween ® 20 | 2.00 |
| Agrimer ® 30 (30% wt/wt solution) | 3.30 |
| D.I. Water | q.s. |
| TOTAL | 100.0 |
| Batch Size, grams | 200.0 |

The composition described in Table 2 when initially evaluated for treating corn seed at concentrations higher than 500 μg/kernel failed to completely dry resulting in seed treatment films that were excessively sticky.

Example 2

Compositions Evaluated in the Development of S-(+)-Abscisic Acid Aqueous Suspension Concentrate (Table 3)

In Example 2-A, a pre-mix in a portion of water was prepared by solubilizing potassium sorbate, tetrasodium EDTA, propyl gallate solution, Agrimer® 30 solution, Tween® 20 and solution of methyl and propyl paraben in propylene glycol. To this, Norlig® A, antifoam 100FG and S-(+)-Abscisic acid were added and mixed. The remaining portion of water was added and wet milled utilizing a Lab-scale Attritor with 2400 g of ⅛ inch stainless steel grinding media. Xanthan gum which was pre-dispersed in a small portion of propylene glycol was added after two hours of wet milling. The milling process was continued for an additional three hours to reduce the particle size. The formulation appeared to be very viscous and not flowable or pourable.

In Example 2-B, the amount of Norlig® A (calcium lignosulfonate) was increased to 3.0% and the amount of Agrimer® 30 solution was decreased to 0.8%. The pre-mix in water was prepared by solubilizing and dispersing potassium sorbate, tetrasodium EDTA, propyl gallate solution, antifoam 100FG, Tween® 20, and S-(+)-Abscisic acid technical powder. To this, Agrimer® 30 solution and an additional two grams of antifoam were added and mixed well. The pre-mix was transferred to Attritor and milled under cold water jacketed condition for five hours. The formulation was very viscous (3120 cP) and foamy.

In Example 2-C, Norlig® A and Tween® 20 were removed from the formula. Two difunctional block copolymer surfactants—Pluronic® 10R5 (with terminal secondary hydroxyl groups) and Pluronic® P104 (with terminal primary hydroxyl groups) were introduced at 5% and 2% weight, respectively. The pre-mix in water was prepared initially by solubilizing and dispersing potassium sorbate, tetrasodium EDTA, propyl gallate solution, antifoam 100FG, Pluronic® 10R5, a mixture of methyl paraben, propyl paraben and xanthan gum in propylene glycol and S-(+)-Abscisic acid technical powder. The pre-mix was charged to an attritor and milled for 4 hours. During milling, liquefied Pluronic® P104 was added and mixed until fully solubilized. The formulation was easily flowable with a viscosity of about 140 cP (at ambient temperature).

TABLE 3

Compositions Evaluated in the Development of S-(+)-Abscisic Acid Aqueous Suspension Concentrate (Example 2)

| Component | 2-A % wt/wt | 2-B % wt/wt | 2-C % wt/wt |
| --- | --- | --- | --- |
| S-(+)-Abscisic acid Technical Grade Active Ingredient, 95.5% Purity | 21.24 | 21.60 | 21.60 |
| Propylene Glycol | 7.87 | 10.00 | 10.00 |
| Xanthan gum | 0.16 | 0.10 | 0.07 |
| Norlig ® A | 1.57 | 3.00 | — |
| Pluronic ® 10R5 | — | — | 5.00 |
| Methyl paraben | 0.16 | 0.20 | 0.25 |
| Propyl paraben | 0.08 | 0.10 | 0.10 |
| Potassium sorbate | 0.20 | 0.25 | 0.25 |
| EDTA, Tetrasodium salt | 0.20 | 0.25 | 0.25 |
| Propyl gallate, 20% | 0.39 | 0.50 | 0.50 |
| Antifoam 100FG | 0.20 | 0.25 | 0.50 |
| Tween ® 20 | 1.57 | 2.00 | — |
| Pluronic P104 | — | — | 2.00 |
| Agrimer ® 30, 30% solution | 2.60 | 0.80 | 0.40 |
| D.I. Water | q.s. | q.s. | q.s. |
| TOTAL | 100.0 | 100.0 | 100.0 |
| Batch Size, grams | 508.1 | 500.0 | 500.0 |

Example 3

Preparation of 25% Wt/Wt S-(+)-Abscisic Acid Aqueous Suspension Concentrate (Table 4)

The composition utilized in the development of an experimental aqueous suspension concentrate formulation containing 25% wt/wt S-(+)-Abscisic acid is shown in Table 4. In this example, a pre-mix in water was prepared by solubilizing and dispersing potassium sorbate, tetrasodium EDTA, propyl gallate, Agrimer® VA6, Pluronic® 10R5, Pluronic® P104, Antifoam SAG 1572 emulsion, and a mixture of propylene glycol, methyl paraben, propyl paraben, and xanthan gum followed by slow addition of 25% wt/wt S-(+)-Abscisic acid technical powder under mixing which is continued until a homogeneous mixture is obtained. The pre-mix was then charged to an Attritor containing 1800 grams of ⅛ inch stainless steel grinding media. The contents were milled until the desired particle size is achieved. Additional antifoam was added and mixed. The suspension was collected by sieving through an appropriate sieve. This formulation showed good flow properties with a viscosity of 415 cP (at 24° C.) and a median particle size of 4.8 micrometers.

TABLE 4

Composition for 25% wt/wt S-(+)-Abscisic Acid Aqueous Suspension Concentrate (Example 3)

| Component | % wt/wt |
| --- | --- |
| S-(+)-Abscisic acid Technical Grade Active Ingredient, 95.5% Purity | 27.00 |
| Propylene Glycol | 10.00 |
| Xanthan gum | 0.10 |
| Pluronic ® 10R5 | 3.00 |
| Methyl paraben | 0.25 |
| Propyl paraben | 0.10 |
| Potassium sorbate | 0.30 |
| EDTA, Tetrasodium salt, Trilon BX Powder | 0.20 |
| Propyl gallate, 20% solution | 0.50 |
| SAG 1572, 30% emulsion | 1.40 |
| Pluronic ® P104 | 3.00 |
| Agrimer ® VA6, 30% solution | 3.30 |
| D.I. Water | q.s. |
| TOTAL | 100.0 |
| Batch Size, grams | 600.0 |

Example 4

Preparation of 25% Wt/Wt S-(+)-Abscisic Acid Aqueous Suspension Concentrate (Table 5)

The general procedure adopted for the formulations described in Table 5 (except for 4-F) is as follows. A pre-mix in water was prepared by solubilizing and dispersing potassium sorbate, tetrasodium EDTA, propyl gallate, Agrimer® VA6, Pluronic® 10R5 and Pluronic® P104/Pluraflo® L1060. The pre-mix contained only half the required amounts of Pluronic® 10R5 and Pluronic® P104. The pre-mix further contained a mixture of propylene glycol, methyl paraben, propyl paraben, a portion of Optixan 40T, and a portion of antifoam emulsion followed by slow incorporation of S-(+)-Abscisic acid under mixing. Mixing was continued until a homogeneous mixture was obtained. The mixture was then passed through DYNO®-Mill MultiLab to achieve the desired particle size range (2 to 8 μm). The remaining portion of antifoam SAG 1572 and Optixan 40T was added and mixed under low shear until a homogenous suspension is obtained. In Example 4-F, in addition to antifoam SAG 1572 and Optixan 40T, the process also included addition of remaining portions of Pluronic® P104 in propylene glycol and Pluronic® 10R5.

The compositions are evaluated as shown in Table 5. In Examples 4-A to 4-F, % wt/wt of preservatives (potassium sorbate, propyl paraben, methyl paraben), chelating agent (EDTA, tetrasodium salt), antifreeze/solubilization aid (propylene glycol), antioxidant (propyl gallate) and binder (Agrimer® VA6) were kept constant.

The formula given in Example 4-A utilized 3% wt/wt each of Pluronic® 10R5 and Pluronic® P104 and 0.09% wt/wt of Optixan 40T (xanthan gum) and 0.5% wt/wt of antifoam SAG 1572. This formula resulted in high initial viscosity of 745 cP. The formula also produced unacceptable amounts of foam during the process.

The formula in Example 4-B included 3% wt/wt of Pluronic® 10R5 and 0.5% wt/wt of antifoam SAG 1572. This formula selectively eliminated use of Pluronic® P104 and Optixan 40T. This formulation had unacceptable viscosity. This demonstrated that Pluronic® 10R5 contributed to high viscosity.

The formula in Example 4-C included 3% wt/wt of Pluronic® 10R5, 0.5% wt/wt of Pluraflo® L1060 (liquid version of Pluronic® P104 equivalent), 0.04% wt/wt of Optixan 40T, and 0.5% of antifoam SAG1572. This formulation had high viscosity as well as high foam.

In Example 4-D, the formulation was prepared utilizing 3% wt/wt of Pluraflo® L1060 (liquid version of Pluronic® P104 equivalent), reduced level of Optixan 40T at 0.02% wt/wt and slightly increased level of antifoam SAG 1572 at 0.6% wt/wt. The formulation thus prepared exhibited lower viscosity of 245 cP but with excessive foam. This formulation demonstrated that Pluronic® P104 contributed to significantly lower viscosity as well as resulting in excessive foam. A slight increase of antifoam SAG 1572 in the formula did not help reduce the foam during the process.

The formula of Example 4-E utilized both Pluronic® 10R5 and Pluraflo® L1060 (Liquid version of Pluronic® P104 equivalent weight of 1.5% each (1:1)). Optixan 40T was kept at 0.04% wt/wt and antifoam SAG 1572 was kept at 0.5% wt/wt. The formulation exhibited high viscosity of 748 cP and excessive foam.

In Example 4-F, both Pluronic® 10R5 and Pluronic® P104 were kept at equivalent weight of 3% each (1:1 ratio). In this Example, Optixan 40T was increased to 0.04% wt/wt and antifoam SAG 1572 was increased to 1.4% wt/wt. This formulation exhibited low viscosity of 272 cP and no significant foam.

The formulas in 4-B to 4-F illustrated the unexpected but significant roles played by both difunctional copolymeric surfactants Pluronic® 10R5 and Pluronic® P104/Pluraflo® L1060. Both these surfactants were shown to be critical in stabilizing S-Abscisic acid in a suspension form, but resulted in formulations with unacceptable physical properties. Interestingly, Pluronic® 10R5 and Pluronic® P104/Pluraflo® L1060 play significantly different roles in S-Abscisic Acid stabilization. Pluronic® 10R5 contributes toward increased viscosity while Pluronic® P104/Pluraflo® L1060 contributes to a significantly lower product viscosity. The Examples 4-E and 4-F demonstrated that the ratio of Pluronic® 10R5 and Pluronic® P104/Pluraflo® L1060 was not as critical as the actual amounts utilized in the formulation. Pluronic® 10R5, due to its ability to impart viscosity during wet milling, facilitates efficient particle size reduction of S-Abscisic acid. On the other hand, Pluronic® P104/Pluraflo® L1060 minimizes potential for excessive viscosity contributed by Pluronic® 10R5 during milling.

TABLE 5

Compositions Evaluated in the Development of S-(+)-Abscisic Acid Aqueous Suspension Concentrate (Example 4)

| Component | 4-A % wt/wt | 4-B % wt/wt | 4-C % wt/wt | 4-D % wt/wt | 4-E % wt/wt | 4-F % wt/wt |
|---|---|---|---|---|---|---|
| S-(+)-Abscisic acid | 25.0 | 25.0 | 25.0 | 25.0 | 25.0 | 25.00 |
| Potassium sorbate | 0.30 | 0.30 | 0.30 | 0.30 | 0.30 | 0.30 |
| EDTA, Tetrasodium salt | 0.20 | 0.20 | 0.20 | 0.20 | 0.20 | 0.20 |
| Propylene glycol | 10.00 | 10.00 | 10.00 | 10.00 | 10.00 | 10.00 |
| Propyl paraben | 0.10 | 0.10 | 0.10 | 0.10 | 0.10 | 0.10 |
| Methyl paraben | 0.20 | 0.20 | 0.20 | 0.20 | 0.20 | 0.20 |
| Xanthan gum | 0.09 | — | 0.04 | 0.02 | 0.04 | 0.04 |
| Propyl gallate, 20% | 0.50 | 0.50 | 0.50 | 0.50 | 0.50 | 0.50 |
| Agrimer® VA6, 20% solution | 4.50 | 4.50 | 4.50 | 4.50 | 4.50 | 4.50 |
| Pluronic® 10R5 | 3.00 | 3.00 | 3.00 | — | 1.50 | 3.00 |
| Pluronic® P104 | 3.00 | — | — | — | — | 3.00 |
| Pluraflo® L1060 | — | — | 0.50 | 3.00 | 1.50 | — |
| SAG 1572 | 0.50 | 0.50 | 0.50 | 0.60 | 0.50 | 1.40 |
| D.I. Water | q.s. | q.s. | q.s. | q.s. | q.s. | q.s. |
| TOTAL | 100.0 | 100.0 | 100.0 | 100.00 | 100.00 | 100.0 |
| Viscosity (cP) @ RT | 745 | Too high | 770 | 245 | 748 | 272 |
| Remarks | Foamy | — | Foamy | Foamy | Foamy | No significant foam |

Example 5

Most Preferred Composition for 25% Wt/Wt S-(+)-Abscisic Acid Aqueous Suspension Concentrate (Table 6)

TABLE 6

Preferred 25% S-(+)-Abscisic Acid Aqueous Suspension Concentrate (Example 5)

| Component | % wt/wt |
|---|---|
| S-(+)-Abscisic acid Technical Grade Active Ingredient, 98.0% Purity | 26.02 |
| Propylene glycol | 10.00 |
| Xanthan gum | 0.06 |
| Pluronic® 10R5 | 0.40 |
| Methyl paraben | 0.20 |
| Propyl paraben | 0.10 |
| Potassium sorbate | 0.30 |
| EDTA, Tetrasodium salt | 0.20 |

TABLE 6-continued

Preferred 25% S-(+)-Abscisic Acid Aqueous Suspension Concentrate (Example 5)

| Component | % wt/wt |
|---|---|
| Propyl gallate as a 20% solution | 0.50 (0.10) |
| SAG 1572, 30% emulsion | 1.40 (0.42) |
| Pluronic ® P104 | 3.00 |
| Agrimer ® VA6 as a 20% solution | 4.50 (0.90) |
| D.I. Water | q.s. |
| TOTAL | 100.0 |
| Batch Size, grams | 6000.0 |

The preferred composition for 25% wt/wt S-(+)-Abscisic acid aqueous suspension concentrate is shown in Table 6. A pre-mix in water was prepared by solubilizing/dispersing potassium sorbate, tetrasodium EDTA, propyl gallate solution, Agrimer VA6 solution, the required amount of Pluronic® 10R5 and ½ the required amount of liquefied Pluronic® P104 in a portion of propylene glycol, and a mixture of propylene glycol, methyl paraben, propyl paraben and a portion of xanthan gum, and a portion of antifoam emulsion followed by slow incorporation of S-(+)-Abscisic acid under mixing. Mixing is continued until a homogeneous mixture is obtained. The mixture is then passed twice through DYNO®-Mill MultiLab (Willy A Bachofen AG, CH4132 Muttenz 1 Switzerland) utilizing 1730 grams of 0.5 MM size very high density zirconium oxide grinding media under glycol-water jacket (−5° C. to 8° C.) to achieve the desired particle size range of 2 to 8 μm. The remaining portions of Pluronic® P104/propylene glycol mix, antifoam emulsion and xanthan gum in propylene glycol are added respectively and mixed under low shear for minimum of two hours. The viscosity of the formulation was 235 cP (at 24.7° C.). The median volume particle size of the milled formulation was 4.5 μm.

The preferred composition exhibited superior compatibility with conventional seed treatment co-formulants (insecticides, fungicides, binders, colorants etc.). The preferred composition of Example 5 when applied either as a foliar spray or sprench (foliar spray and soil drench) surprisingly showed substantial superior biological performance compared to S-(+)-Abscisic acid and S-(+)-Abscisic acid salt.

The preferred composition has a viscosity that is flowable for easy handling, mixing, and application, and maintains suspension stability.

Applicants found throughout their numerous studies that each component contributed to the unique properties of the formulation. In addition, Applicants found that the amount of surfactant with secondary hydroxyl groups (Pluronic® 10R5) was critical for the proper viscosity of the formulation. Further, the amount of rheological additive (xanthan gum) was important for the formulation to have the appropriate qualities. Applicants also found that the amount of the silicone antifoam (SAG 1572) was critical for reducing foam. The previous formulations had too much foam which was detrimental to the physical properties of the formulations.

Example 6

Accelerated Stability Study

A study to determine the accelerated stability of the aqueous flowable suspension concentrate was conducted in 125 mL PET bottles. The data on the S-(+)-Abscisic acid content at the initial reading (T=0) and 2 weeks later at 54° C. averaged over five lots are presented in Table 7. The data reveal that the amount of S-(+)-Abscisic acid remained stable during a high temperature exposure over a two week period.

TABLE 7

Accelerated Stability Data

| Station | Assay (% S-(+)-Abscisic acid) | Mean |
|---|---|---|
| T = 0 | 26.2 | 26.28 |
| 2 wk @ 54° C. | 26.1 | 26.74 |

Example 7

Composition for 5% Wt/Wt S-(+)-Abscisic Acid Aqueous Suspension Concentrate (Table 8)

A composition developed for 5% wt/wt S-(+)-Abscisic acid aqueous suspension concentrate is shown in Table 8. A pre-mix in water was prepared by solubilizing/dispersing potassium sorbate, tetrasodium EDTA, propyl gallate solution, Agrimer® VA6 solution, the required amount of Pluronic® 10R5 and ½ the required amount of liquefied Pluronic® P104 in a portion of propylene glycol, and a mixture of propylene glycol, methyl paraben, propyl paraben and a portion of xanthan gum, and a portion of antifoam emulsion followed by slow incorporation of S-(+)-Abscisic acid under mixing. Mixing is continued until a homogeneous mixture is obtained. The mixture is then passed twice through DYNO®-Mill MultiLab (Willy A Bachofen AG, CH4132 Muttenz 1 Switzerland) utilizing 1725.44 grams of 0.5 MM size very high density zirconium oxide grinding media under glycol-water jacket (0° C. to 4° C.) to achieve the desired particle size range of 2 to 8 μm. The remaining portions of Pluronic® P104/propylene glycol mix, antifoam emulsion and xanthan gum in propylene glycol are added respectively and mixed under low shear for a minimum of two hours. The viscosity of the formulation was 710 cP (at 19.5° C.). The median volume particle size of the milled formulation was 4.6 to 4.9 μm.

TABLE 8

Preferred 5% wt/wt S-(+)-Abscisic Acid Aqueous Suspension Concentrate (Example 7)

| Component | % wt/wt |
|---|---|
| S-(+)-Abscisic acid Technical Grade Active Ingredient, 98.0% Purity | 5.36 |
| Propylene glycol | 10.00 |
| Xanthan gum | 0.30 |
| Pluronic ® 10R5 | 0.60 |
| Methyl paraben | 0.20 |
| Propyl paraben | 0.10 |
| Potassium sorbate | 0.30 |
| EDTA, Tetrasodium salt | 0.20 |
| Propyl gallate as a 20% solution | 0.50 (0.10) |
| SAG 1572, 30% emulsion | 1.40 (0.42) |
| Pluronic ® P104 | 0.60 |
| Agrimer ® VA6 as a 20% solution | 4.50 (0.90) |
| D.I. Water | q.s. |
| TOTAL | 100.0 |
| Batch Size, grams | 1500.0 |

Example 8

Composition for 10% Wt/Wt S-(+)-Abscisic Acid Aqueous Suspension Concentrate (Table 9)

A composition developed for 10% wt/wt S-(+)-Abscisic acid aqueous suspension concentrate is shown in Table 9. A pre-mix in water was prepared by solubilizing/dispersing potassium sorbate, tetrasodium EDTA, propyl gallate solution, Agrimer® VA6 solution, the required amount of Pluronic® 10R5 and ½ the required amount of liquefied Pluronic® P104 in a portion of propylene glycol, and a mixture of propylene glycol, methyl paraben, propyl paraben and a portion of xanthan gum, and a portion of antifoam emulsion followed by slow incorporation of S-(+)-Abscisic acid under mixing. Mixing was continued until a homogeneous mixture was obtained. The mixture is then passed twice through DYNO®-Mill MultiLab (Willy A Bachofen AG, CH4132 Muttenz 1 Switzerland) utilizing 1725.44 grams of 0.5 MM size very high density zirconium oxide grinding media under glycol-water jacket (0° C. to 1° C.) to achieve the desired particle size range of 2 to 8 μm. The remaining portions of Pluronic® P104/propylene glycol mix, antifoam emulsion and xanthan gum in propylene glycol are added respectively and mixed under low shear for a minimum of two hours. The viscosity of the formulation was 272 cP (at 22.8° C.). The median volume particle size of the milled formulation was 4.88 μm.

TABLE 9

Preferred 10% wt/wt S-(+)-Abscisic Acid Aqueous Suspension Concentrate (Example 8)

| Component | % wt/wt |
| --- | --- |
| S-(+)-Abscisic acid Technical Grade Active Ingredient, 98.0% Purity | 10.71 |
| Propylene glycol | 10.00 |
| Xanthan gum | 0.16 |
| Pluronic ® 10R5 | 0.60 |
| Methyl paraben | 0.20 |
| Propyl paraben | 0.10 |
| Potassium sorbate | 0.30 |
| EDTA, Tetrasodium salt | 0.20 |
| Propyl gallate as a 20% solution | 0.50 (0.10) |
| SAG 1572, 30% emulsion | 1.40 (0.42) |
| Pluronic ® P104 | 1.00 |
| Agrimer ® VA6 as a 20% solution | 4.50 (0.90) |
| D.I. Water | q.s. |
| TOTAL | 100.0 |
| Batch Size, grams | 1500.0 |

Example 9

Composition Developed for 24.92% Wt/Wt S-(+)-Abscisic Acid and 0.83% Wt/Wt 6-Benzyl Adenine (6-BA) Aqueous Suspension Concentrate (Table 10)

A composition developed for 24.92% wt/wt S-(+)-Abscisic acid and 0.83% 6-BA aqueous suspension concentrate is shown in Table 10. 6-BA was incorporated into the pre-mix after introduction of S-(+)-Abscisic acid into the pre-mix. The procedure for producing this formulation was similar to the detailed procedure provided in Example 4. The batch size for this formulation was 4000 grams. The viscosity of the formulation was 312 cP (at 22.4° C.) and the pH was 5.22.

TABLE 10

24.92% wt/wt S-(+)-Abscisic acid and 0.83% wt/wt 6-benzyl adenine Aqueous Suspension Concentrate (Example 9)

| Component | % wt/wt |
| --- | --- |
| S-(+)-Abscisic acid Technical Grade Active Ingredient, 98.0% Purity | 25.43 |
| 6-benzyl adenine Technical Grade Active Ingredient, 99.6% Purity | 0.84 |
| Propylene glycol | 10.00 |
| Xanthan gum | 0.06 |
| Pluronic ® 10R5 | 0.40 |
| Atlox Metasperse 500L | 0.50 |
| Methyl paraben | 0.20 |
| Propyl paraben | 0.10 |
| Potassium sorbate | 0.30 |
| EDTA, Tetrasodium salt | 0.20 |
| Propyl gallate as a 20% solution | 0.50 (0.10) |
| SAG 1572, 30% emulsion | 1.40 (0.42) |
| Pluronic ® P104 | 3.00 |
| Agrimer ® VA6 as a 20% solution | 4.50 (0.90) |
| D.I. Water | q.s. |
| TOTAL | 100.0 |
| Batch Size, grams | 4000.0 |

Example 10

Methods for Treating Seeds

For seed treatment the compositions of the invention are diluted to the desired amount of S-(+)-Abscisic acid concentration with a sufficient amount of water. Depending on the batch size, this diluted spray volume is then sprayed onto seeds in a seed treater either as a single batch or multiple batches. Considering that the total amount of water added to the seed is minimal, no drying step is required prior to packaging and storage. The above procedure in general can be either scaled up or down depending on the batch size of seeds to be treated.

A standard pesticidal package will typically be used with the suspension concentrate. These pesticides, including fungicides and insecticides can either be incorporated into the seed treatment compositions of the invention or applied separately to the seed prior to treatment.

The compositions of the invention adhered promptly to seed without exhibiting any symptoms of stickiness or peel-off from the seed upon storage and handling. The compositions not only exhibit the desired germination delay but also do not exhibit any deleterious effect on the seed quality even after extended storage. In addition, the formulations are highly compatible with various seed treatment mixtures and still results in typical germination delay response.

Example 11

Growth Chamber Study

A seed treatment experiment was conducted on five male parent inbreds, pretreated with fungicides and insecticide, commonly used in hybrid seed production at five different dosages (0, 75, 150, 300, and 600 μg S-(+)-Abscisic acid/kernel) by the procedure described in Example 10. Five doses were applied to samples of each inbred, by including different amounts of the suspension concentrate in the seed treatment slurry.

Soil trays were filled to 3 cm from the top using a fine-textured field soil that was moistened to 19% wt/wt moisture content. Fifty pre-counted seeds were placed onto the soil surface and covered with additional soil to make the overall tray weight 1 kilogram. The soil in the box was gravimetrically adjusted to 21% moisture by sprinkling water on the surface. These soil trays were transferred into large transparent plastic boxes with close-fitting transparent lids and placed under continuous light (standard 2-bulb fluorescent fixtures) in a controlled temperature chamber maintained at 18° C. The soil temperature inside the chamber averaged about 20° C.

The soil trays were monitored gravimetrically and watered on a daily basis to maintain moisture content of 21%. Once emergence began, counts were taken daily. As the pace of emergence slowed, the counts were made at progressively longer intervals, so that by the end of the germination period (44 days) counts were made every 3 to 4 days. At each count, the soil tray was monitored gravimetrically and watered to maintain soil moisture at 21%. As the plants became large, the amount of water added is increased to roughly correct for the weight of the plants. The plants were periodically trimmed to ensure accurate maintenance of soil moisture. Each tray was terminated when the emergence reached 50 and/or no further emergence was observed for 10 days.

To the data from each experimental unit, a two-parameter cumulative Gompertz model was fitted using SAS Proc NLIN. Only seeds that ultimately germinated were included in the model (by fitting the model only to the germinants, T50 and final stand are made orthogonal). From the model parameters for each unit, the median time to emergence and the difference in days between the $10^{th}$ and the $90^{th}$ percentiles, which is a measure of the width of the emergence distribution (the 10-90 range), were calculated. Final emergence was calculated as a percentage based on the number of seeds planted.

Table 11 demonstrates that seed treatment with the suspension concentrate of the invention effectively delays germination and emergence of corn seeds planted in field soil. Emergence of the seedlings is delayed up to 20 days beyond the emergence of untreated seed.

TABLE 11

Average Time to Emerge from 5 inbred lines treated with S-(+)-Abscisic acid Suspension Concentrate and Germinated in Soil Boxes at 20° C.

| Inbred | S-(+)-Abscisic acid dose (μg/kernel) | Median emergence time (days) |
|---|---|---|
| A | 0 | 6.6 |
| A | 75 | 17.9 |
| A | 150 | 21.5 |
| A | 300 | 25.5 |
| A | 600 | 28.9 |
| B | 0 | 6.8 |
| B | 75 | 14.8 |
| B | 150 | 16.6 |
| B | 300 | 19.4 |
| B | 600 | 23.5 |
| C | 0 | 6.1 |
| C | 75 | 12.9 |
| C | 150 | 15.6 |
| C | 300 | 17.8 |
| C | 600 | 20.4 |
| D | 0 | 7.5 |
| D | 75 | 15.7 |
| D | 150 | 19.7 |
| D | 300 | 23.0 |
| D | 600 | 27.4 |
| E | 0 | 6.2 |
| E | 75 | 11.0 |
| E | 150 | 12.9 |
| E | 300 | 16.6 |
| E | 600 | 22.4 |

Example 12

Field Trial

A scaled-up experiment was set up in the field and seeds were treated as in Example 10. Planting was carried out at three different dates in Central Illinois. At each planting date, the trial was laid out as a split-plot, with inbred as the main-plot and dose-within-inbred as the sub-plot factor. The treatments were arranged in a randomized complete block design and 2 replications were performed. Each plot consisted of two rows 20 feet long into which about 60 kernels were planted to a depth of about 2 inches employing a small plot planter.

At the beginning of anthesis, the number of plants shedding pollen in each plot was counted daily, until all the plants in the trial had shed pollen. The time until 10, 50, and 90% of the plants were shedding pollen was determined to the nearest day.

Table 12 demonstrates the effect of the S-(+)-Abscisic acid suspension concentrate of the invention on flowering time of typical male parents used in hybrid corn seed production. Economically useful delays were obtained from treating seed with the S-(+)-Abscisic acid suspension concentrate.

TABLE 12

Average Number of Days Delay in Median Anthesis for Inbred Corn Seed Treated with S-(+)-Abscisic acid Suspension Concentrate Formulation

| Inbred | S-(+)-Abscisic acid dose (μg/kernel) | Delay at anthesis from different planting dates | | |
|---|---|---|---|---|
| | | 1 | 2 | 3 |
| A | 0 | 0.0 | 0.0 | 0.0 |
| A | 75 | 4.0 | 2.0 | 4.0 |
| A | 150 | 4.5 | 3.5 | 5.0 |
| A | 300 | 5.5 | 5.0 | 8.5 |
| A | 600 | 7.0 | 6.5 | 10.5 |
| B | 0 | 0.0 | 0.0 | 0.0 |
| B | 75 | 1.0 | 1.0 | 1.0 |
| B | 150 | 1.0 | 1.5 | 2.0 |
| B | 300 | 3.5 | 2.0 | 3.5 |
| B | 600 | 3.0 | 3.0 | 4.0 |
| C | 0 | 0.0 | 0.0 | 0.0 |
| C | 75 | 1.5 | 1.0 | 3.0 |
| C | 150 | 3.0 | 2.0 | 5.0 |
| C | 300 | 3.0 | 2.5 | 7.5 |
| C | 600 | 4.0 | 4.5 | 8.5 |
| D | 0 | 0.0 | 0.0 | 0.0 |
| D | 75 | 2.5 | 1.5 | 2.0 |
| D | 150 | 5.5 | 4.0 | 4.0 |

TABLE 12-continued

Average Number of Days Delay in Median Anthesis
for Inbred Corn Seed Treated with S-(+)-Abscisic
acid Suspension Concentrate Formulation

| Inbred | S-(+)-Abscisic acid dose (μg/kernel) | Delay at anthesis from different planting dates | | |
|---|---|---|---|---|
| | | 1 | 2 | 3 |
| D | 300 | 5.5 | 5.0 | 4.5 |
| D | 600 | 8.5 | 6.0 | 4.5 |
| E | 0 | 0.0 | 0.0 | 0.0 |
| E | 75 | 2.0 | 6.0 | 4.0 |
| E | 150 | 1.5 | 7.0 | 7.5 |
| E | 300 | 2.0 | 9.0 | 8.0 |
| E | 600 | 4.0 | 9.5 | 10.5 |

Example 13

Tomato Transpiration Inhibition Study

The inhibition of transpiration by the stomata closure reduces the water loss in plant leaf cell. During drought stress conditions, the reduction of water loss facilitated by transpiration inhibition will help maintain water status and physiological function within the plant. Therefore, it is extremely important for plants to survive in drought stress.

Efficacy of the preferred composition of the present invention was studied with tomato plants to compare its transpiration inhibition effect against 10% potassium salt of S-(+)-Abscisic acid solution (ABA salt) and technical grade active ingredient of the free acid (S-(+)-Abscisic acid).

Tomato (variety: Rutgers) seeds were sown in an 18-cell flat filled with Promix PGX (available from Premier Horticulture Inc. Quakertown, Pa.) for four weeks for germination and initial growth. Plants were then transplanted into pots (18 cm in diameter and 18 cm in height) filled with Promix BX (available from Premier Horticulture Inc. Quakertown, Pa.) and grown for another 5 days before treatment. During growing periods, plants received daily irrigation and weekly fertilizer (1 g/L all purpose fertilizer 20-20-20, The Scotts Company, Marysville, Ohio).

S-(+)-Abscisic acid solutions of different formulations were foliar applied to tomato plant leaves at the rate of 24 mL/6 plants. Plants were then placed in a transparent chamber with humidity controlled at relative humidity 40 to 60%. Leaf transpiration rate was measured 1, 2, 3 or 4 and 7 days after treatment using an AP4 Leaf Porometer (Dynamax, Inc., Houston, Tex.). The transpiration rate of each treatment was calculated as the percentage of that of control at each day to reduce day-to-day variation caused by changes of environmental condition such as light intensity and temperature. The log-linear regression between S-(+)-Abscisic acid doses and the average transpiration rates of first 3 days after treatment was used for calculation of S-(+)-Abscisic acid dose to achieve 50% inhibition of transpiration.

Results presented in Table 13 indicated a strong negative correlation between log of S-(+)-Abscisic acid dose applied to tomato leaves and the transpiration rate of the plants. S-(+)-Abscisic acid doses to achieve 50% inhibition of transpiration were 7.98, 10.13, and 15.02 mg/plant for the composition of the invention, S-(+)-Abscisic acid salt, and S-(+)-Abscisic acid, respectively. Surprisingly, the efficacy of the composition of the invention is 1.27 times as much as S-(+)-Abscisic acid salt and 1.88 times as much as S-(+)-Abscisic acid over first 3 days after treatment. Thus, when S-(+)-Abscisic acid is foliar applied, efficacy of the preferred composition of the present invention is superior to S-(+)-Abscisic acid salt and S-(+)-Abscisic acid in terms of tomato leaf transpiration inhibition.

TABLE 13

Relative Effect of the Preferred Composition of the Invention,
S-(+)-Abscisic acid salt, and S-(+)-Abscisic acid on
Transpiration Inhibition When Foliarly Applied to Tomato Leaves

| | | Transpiration rate (% of control) Average of 3 days after treatment | | |
|---|---|---|---|---|
| ABA dose (mg) | Log [ABA] | Preferred Composition | S-(+)-Abscisic acid salt | S-(+)-Abscisic acid |
| 1 | 0.00 | 68 | 70 | 73 |
| 3 | 0.48 | 58 | 60 | 63 |
| 10 | 1.00 | 48 | 50 | 54 |
| Equation | | y = 68 − 20x | y = 70 − 20x | y = 73 − 20x |
| $R^2$ | | 1.00 | 1.00 | 1.00 |
| S-(+)-Abscisic acid dose to achieve 50% inhibition of transpiration (mg) | | 7.98 | 10.13 | 15.02 |
| Relative potency | | 1.27 1.88 | 1 | 1 |

Example 14

Pansy Shelf Life Extension Study

Efficacy of the preferred composition of the present invention was also studied with Pansy plants to compare its shelf life extension effect against 10% potassium salt of S-(+)-Abscisic acid solution (ABA salt) and technical grade active ingredient of the free acid (S-(+)-Abscisic acid).

Pansy plants were obtained from local retailers as mature plants. Pansy plants were then transplanted into an 18-cell flat filled with Promix BX (available from Premier Horticulture Inc. Quakertown, Pa.) and grown for 3 days prior to treatment.

Uniform plants were selected for the study. Prior to S-(+)-Abscisic acid treatment, plants were saturated with water and then drained for about two hours. A total of 20 mL S-(+)-Abscisic acid solution, which is equivalent to about 10% of the cell volume, was applied to each plant by soil drench/foliar spray application. In the ornamental industry, this method of chemical application is commonly known as a sprench application. In this study, 17 mL solution was drench applied to root zone and 3 mL solution was foliar applied to canopy. Plants were not watered following the S-(+)-Abscisic acid treatment.

After the S-(+)-Abscisic acid treatment, plants were arranged in a randomized complete block experimental design. The plants were rated daily for the extent of wilting on a scale from 1 for no wilting to 4 for complete wilting. A rating of 2.5 was the point at which a plant was determined to be unmarketable and the previous day was recorded as the shelf life of that plant in days. The log-linear regression between S-(+)-Abscisic acid doses and the extension of shelf life over control plants was used for calculation of S-(+)-Abscisic acid dose to extend 1 day or 2 days of shelf life.

Results in Table 14 indicated the composition of the invention, S-(+)-Abscisic acid salt, and S-(+)-Abscisic acid extended Pansy shelf life with a log dose manner. S-(+)-Abscisic acid dose to extend 1 day shelf life was 1.95, 2.83, and 8.68 mg/plant for the composition of the invention, S-(+)-Abscisic acid salt, and S-(+)-Abscisic acid, respectively. Unexpectedly, the composition of the invention is 1.45 times as strong as S-(+)-Abscisic acid salt and 4.45 times as strong as S-(+)-Abscisic acid. The pattern to extend 2 days of shelf life is similar. Thus, when S-(+)-Abscisic acid is drench/foliar applied, efficacy of the composition of the invention is also superior to S-(+)-Abscisic acid salt and S-(+)-Abscisic acid.

TABLE 14

Relative Shelf Life Extension Achieved When the Preferred Composition of the Invention, S-(+)-Abscisic acid salt and S-(+)-Abscisic acid are Drench and Foliar Applied

| | | Days of extended shelf life | | |
|---|---|---|---|---|
| ABA dose (mg) | Log [ABA] | Preferred Composition | S-(+)-Abscisic acid salt | S-(+)-Abscisic acid |
| 1 | 0.00 | 0.67 | 0.50 | 0 |
| 3 | 0.48 | 1.33 | 1.17 | 0.67 |
| 10 | 1.00 | 1.50 | 1.50 | 0.83 |
| 30 | 1.48 | 2.00 | 1.83 | 1.67 |
| Equation | | y = 0.76 − 0.84x | y = 0.61 − 0.87x | y = 0.03 − 1.04x |
| $R^2$ | | 0.95 | 0.96 | 0.90 |
| S-(+)-Abscisic acid dose (mg) to extend 1 day of shelf life | | 1.95 | 2.83 | 8.68 |
| Relative potency (1 day) | | 1.45 4.45 | 1 | 1 |
| S-(+)-Abscisic acid dose (mg) to extend 2 days of shelf life | | 30.61 | 39.83 | 79.62 |
| Relative potency (2 days) | | 1.30 2.60 | 1 | 1 |

Example 15

In this example, the effect of the cytokinin 6-benzyladenine on S-(+)-Abscisic acid induced germination delay on Canola was studied. The experiment was set up as an S-(+)-Abscisic acid-dose×BA-dose factorial experiment, with four doses of S-(+)-Abscisic acid (0, 25, 50, and 100 g/cwt) and four doses of 6-benzyladenine (0, 1, 5 and 25 g/cwt) for a total of 16 treatment combinations. The treatments were made up in 1 ml samples of experimental aqueous seed treatment slurry. S-(+)-Abscisic acid was added in the form of a water solution of the ammonium salt. 6-Benzyladenine was added as technical powder. Ten µl Tween® 20 were added to each sample to help wet and suspend the 6-benzyladenine powder. All of the seed treatment slurry samples contained CF-Clear film-forming agent and Color Coat Red (available from Becker Underwood), each at 1 oz/cwt, and 0.167 oz/cwt Maxim XL fungicide (available from Syngenta). The slurry application volume was 40 oz/cwt (cwt means per 100 lbs or 45.4 kgs of seed). Ten gram samples of canola seed were treated with the experimental slurries using a Hege 11 seed treater with a six-inch bowl.

The seed was planted in plastic boxes containing 1 kg of typical agricultural silt loam. One hundred seeds were planted 2 cm deep in each plastic box, and the soil in the box was adjusted to 21% soil moisture (wet-weight basis). Two replications of the experiment were incubated under constant light in a 10° C. chamber. The soil temperature averaged 12.6° C. The boxes were watered up to the correct weight every 1 to 2 days, and checked for emergence. Counts of seedlings were continued until it became clear that emergence had ceased (28 days). The final count of emerged seedlings was expressed as a percentage of the 100 seeds planted.

The daily counts were converted to proportions of the final emergence of the box, and a Gompertz curve was fitted to the data from each box using SAS Proc NLIN. From the parameters of the model, median emergence time (T50) and quartile range (Qrange) were estimated for each box. Analysis of variance was performed and means calculated for each of the three responses (Final emergence, T50, Qrange).

As the dose of S-(+)-Abscisic acid was increased from zero to 100 g/cwt, the final emergence declined, and was roughly cut in half at a dose of 100 g/cwt (Table 15). Surprisingly, addition of 6-benzyladenine prevented loss of final emergence that resulted from high doses of S-(+)-Abscisic acid. No significant effect on median-time-to-emergence occurred from 6-benzyladenine addition.

TABLE 15

The Effect of Including 6-benzyladenine Technical Powder in S-(+)-Abscisic Acid Seed Treatments on Emergence of Canola

| S-(+)-Abscisic acid dose (g/cwt) | 6-Benzyladenine dose (g/cwt) | Final emergence (%) | T50 (days) | Qrange (days) |
|---|---|---|---|---|
| 0 | 0 | 99.0 | 6.34 | 1.88 |
| 0 | 1 | 98.0 | 6.37 | 1.30 |
| 0 | 5 | 91.6 | 6.76 | 2.36 |
| 0 | 25 | 89.9 | 7.88 | 3.02 |
| 25 | 0 | 92.3 | 9.15 | 3.26 |
| 25 | 1 | 89.8 | 9.07 | 3.06 |
| 25 | 5 | 94.5 | 8.99 | 3.18 |
| 25 | 25 | 91.1 | 9.64 | 3.80 |
| 50 | 0 | 68.9 | 11.20 | 4.27 |
| 50 | 1 | 88.9 | 10.07 | 4.00 |
| 50 | 5 | 90.2 | 10.73 | 4.27 |
| 50 | 25 | 91.7 | 11.52 | 4.72 |
| 100 | 0 | 53.5 | 12.74 | 4.27 |
| 100 | 1 | 85.4 | 13.20 | 5.23 |
| 100 | 5 | 96.0 | 11.73 | 4.34 |
| 100 | 25 | 84.0 | 12.99 | 4.99 |

We claim:

1. A method of treating a seed comprising applying an aqueous suspension concentrate composition to a seed, wherein the composition comprises:
   from about 5 to about 40% S-(+)-Abscisic acid suspended as micro particles wherein at least 90% of the micro S-(+)-Abscisic acid particles are less than 10 micrometers in diameter;

(ii) from about 0.1 to about 1.0% of at least one non-ionic polymeric surfactant that is a difunctional block copolymer surfactant with terminal secondary hydroxyl groups;

(iii) from about 0.5 to about 4.0% of at least one non-ionic polymeric surfactant that is a difunctional block copolymer surfactant with terminal primary hydroxyl groups;

(iv) from about 0.5 to about 5.0% of at least one vinylpyrrolidone/vinylacetate copolymer wherein the molar ratio of vinylpyrrolidone to vinylacetate is from about 30:70 to about 70:30;

(v) from about 5 to about 20% of at least one diol;

(vi) from about 0.045 to about 0.2% of at least one polysaccharide or cellulose derivative;

(vii) from about 0.01 to about 0.5% of polydimethylsiloxane;

(viii) at least one preservative selected from the group consisting of methyl p-hydroxy benzoate, propyl p-hydroxy benzoate and potassium sorbate;

(ix) at least one chelating agent selected from the group consisting of EDTA, EDTA salts, citrates and gluconates; and (x) at least one antioxidant selected from the group consisting of propyl gallate, ascorbic acid and its salts and tert-butylhydroquinone, wherein all percentages are based on the total weight of the composition.

2. The method of claim 1 wherein the seed includes corn, sorghum, barley, wheat, rice, canola, soybean, peanut, sunflower, beans, carrot, spinach, or tomato.

3. The method of claim 1 wherein the composition is applied in an effective amount to male inbred corn line seeds to alter the timing of germination and tassel development of the seeds to facilitate hybrid seed production.

4. The method of claim 1 wherein the composition is applied in an effective amount to canola seed to achieve germination delay with ultimate higher emergence.

5. The method of claim 1 wherein the composition is applied in an effective amount to the seed to regulate germination.

6. The method of claim 1 wherein the composition is applied in an effective amount to the seed to improve drought stress tolerance, shelf life, quality and yield of crops grown from the seed.

7. The method of claim 1 wherein the composition is applied through foliar, drench, in-furrow or sprench application.

8. The method of claim 1 wherein the S-(+)-Abscisic acid is from about 20 to about 30% wt/wt of the composition.

9. The method of claim 1 wherein the at least one non-ionic polymeric surfactant that is a difunctional block copolymer surfactant with terminal secondary hydroxyl groups is from about 0.20 to about 0.60% wt/wt of the composition.

10. The method of claim 1 wherein the vinylpyrrolidone/vinylacetate copolymer is from about 0.5 to about 1.0% wt/wt of the composition.

11. The method of claim 1 wherein the polysaccharide or cellulose is from about 0.05 to about 0.2% wt/wt of the composition.

12. The method of claim 1 wherein the diol is selected from the group consisting of ethylene glycol, diethylene glycol, propylene glycol and hexylene glycol.

13. The method of claim 1 wherein the diol is propylene glycol and the polysaccharide is xanthan gum.

14. The method of claim 1 wherein the chelating agent is EDTA and the antioxidant is propyl gallate.

15. The method of claim 1 wherein the composition comprises (i) from about 20 to about 30% S-(+)-Abscisic acid;

(ii) from about 0.3 to about 0.5% of the non-ionic polymeric surfactant that is a difunctional block copolymer surfactant with terminal secondary hydroxyl groups;

(iii) from about 2.0 to about 4.0% of the non-ionic polymeric surfactant that is a difunctional block copolymer surfactant with terminal primary hydroxyl groups;

(iv) from about 0.5 to about 1.0% vinylpyrrolidone/vinylacetate copolymer;

(v) from about 5.0 to about 11.0% propylene glycol;

(vi) from about 0.05 to about 0.07% xanthan gum;

(vii) from about 0.3 to about 0.5% polydimethylsiloxane;

(viii) from about 0.1 to about 0.3% methyl p-hydroxy benzoate, from about about 0.08 to about 0.12% propyl p-hydroxy benzoate, and from about 0.25 to about 0.40% potassium sorbate;

(ix) from about 0.1 to about 0.3% EDTA; and (x) from about 0.05 to about 0.12% propyl gallate;

wherein all percentages are based on the total weight of the composition.

16. The method of claim 1 wherein the composition comprises (i) about 25% of S-(+)-Abscisic acid;

(ii) about 0.40% of the non-ionic polymeric surfactant that is a difunctional block copolymer surfactant with terminal secondary hydroxyl groups;

(iii) about 3.00% of the non-ionic polymeric surfactant that is a difunctional block copolymer surfactant with terminal primary hydroxyl groups;

(iv) about 0.90% vinylpyrrolidone/vinylacetate copolymer;

(v) about 10.00% propylene glycol;

(vi) about 0.06% xanthan gum;

(vii) about 0.42% polydimethylsiloxane;

(viii) about 0.20% methyl p-hydroxy benzoate, about 0.10% propyl p-hydroxy benzoate, and about 0.30% potassium sorbate;

(ix) about 0.20% EDTA; and (x) about 0.10% propyl gallate;

wherein all percentages are based on the total weight of the composition.

17. The method of claim 1 wherein the suspension concentrate further comprises a cytokinin selected from the group consisting of 6-benzyladenine, kinetin, zeatin, thidazuron, and forchlorfenuron.

18. The method of claim 17 wherein the cytokinin is 6-benzyladenine.

19. The method of claim 17 wherein the weight ratio of S-(+)-Abscisic acid to the cytokinin is from about 5:1 to about 40:1.

* * * * *